United States Patent
Driemel (10) Patent No.: US 10,004,423 B2
(45) Date of Patent: Jun. 26, 2018

(54) LOCAL COIL AND LEVELING MIRROR

(71) Applicant: Daniel Driemel, Oederan (DE)

(72) Inventor: Daniel Driemel, Oederan (DE)

(73) Assignee: Siemens Aktiengesellschaft, München (DE)

( * ) Notice: Subject to any disclaimer, the term of this patent is extended or adjusted under 35 U.S.C. 154(b) by 232 days.

(21) Appl. No.: 14/471,177

(22) Filed: Aug. 28, 2014

(65) Prior Publication Data

US 2015/0065852 A1 Mar. 5, 2015

(30) Foreign Application Priority Data

Sep. 3, 2013 (DE) .................. 10 2013 217 561

(51) Int. Cl.
*A61B 5/055* (2006.01)
*G01R 33/48* (2006.01)
*G01R 33/34* (2006.01)
*A61B 5/00* (2006.01)

(52) U.S. Cl.
CPC ............ *A61B 5/055* (2013.01); *A61B 5/0555* (2013.01); *A61B 5/6814* (2013.01); *G01R 33/34046* (2013.01); *G01R 33/34084* (2013.01); *G01R 33/34092* (2013.01); *G01R 33/4806* (2013.01)

(58) Field of Classification Search
None
See application file for complete search history.

(56) References Cited

U.S. PATENT DOCUMENTS

| | | | | |
|---|---|---|---|---|
| 2,444,280 A | * | 6/1948 | Burhans | G10D 3/046 84/294 |
| 4,650,299 A | | 3/1987 | Stevens et al. | |
| 4,852,265 A | * | 8/1989 | Rando | G01C 15/002 33/227 |
| 5,075,977 A | * | 12/1991 | Rando | G01B 3/00 33/227 |
| 5,299,769 A | * | 4/1994 | Reusche | A01K 45/002 24/490 |
| 5,305,750 A | * | 4/1994 | Makita | G01R 33/56391 128/118.1 |
| 5,450,690 A | * | 9/1995 | Elsea | A01G 5/04 220/476 |
| 5,819,426 A | * | 10/1998 | Virtanen | G01C 21/203 33/1 G |
| 5,825,563 A | * | 10/1998 | Anand | A61B 5/0555 359/872 |

(Continued)

FOREIGN PATENT DOCUMENTS

DE 10314215 B4 11/2006

OTHER PUBLICATIONS

Ball bearing by Wikipedia, published online on Aug. 26, 2013 at https://en.wikipedia.org/w/index.php?title=Ball_bearing &oldid=570325005; accessed Jun. 6, 2016.*

(Continued)

*Primary Examiner* — Katherine Fernandez
*Assistant Examiner* — Michael Kellogg
(74) *Attorney, Agent, or Firm* — Lempia Summerfield Katz LLC (57) ABSTRACT

The embodiments relate to a local coil arrangement for an imaging MRI system, where the system is a head local coil or a head/neck local coil, which includes a mirror housing that is mounted in a rotatable manner on the local coil arrangement.

21 Claims, 5 Drawing Sheets

(56) References Cited

U.S. PATENT DOCUMENTS

| | | | |
|---|---|---|---|
| 6,352,233 B1* | 3/2002 | Barberich | A47B 21/0314 |
| | | | 248/456 |
| 6,433,548 B1 | 8/2002 | Furuta et al. | |
| 6,774,929 B1 | 8/2004 | Kopp | |
| 6,943,551 B2 | 9/2005 | Eberler et al. | |
| 2003/0061720 A1* | 4/2003 | Waibel | G01C 15/004 |
| | | | 33/281 |
| 2006/0010597 A1* | 1/2006 | Wilson | A61G 7/1015 |
| | | | 5/83.1 |
| 2008/0024133 A1* | 1/2008 | Vaughan | G01R 33/34 |
| | | | 324/318 |

OTHER PUBLICATIONS

Plain bearing by Wikipedia, published online on Aug. 12, 2013 at https://en.wikipedia.org/w/index.php?title=Plain_bearing&oldid=568156060; accessed Jun. 6, 2016.*

Graduation (instrument) by Wikipedia, published online on Mar. 17, 2013 at https://en.wikipedia.org/w/index.php?title=Graduation_(instrument)&oldid=544982016; accessed on Jun. 6, 2016.*

Blinky 3H by planet bike; pub. online at http://ecom1.planetbike.com/3010.html on Nov. 23, 2007.*

German Office Action dated Mar. 21, 2014 for corresponding German Patent Application No. DE 10 2013 217 561.2 with English translation.

* cited by examiner

LOCAL COIL AND LEVELING MIRROR

CROSS-REFERENCE TO RELATED APPLICATIONS

This application claims the benefit of DE 10 2013 217 561.2, filed on Sep. 3, 2013, which is hereby incorporated by reference in its entirety.

TECHNICAL FIELD

The embodiments relate to a local coil.

BACKGROUND

Magnetic resonance imaging (MRI) devices for examining objects or patients by magnetic resonance imaging are described in, e.g., DE 10 314 215 B4.

SUMMARY

It is an object of the present embodiments to optimize a local coil. The scope of the present invention is defined solely by the appended claims and is not affected to any degree by the statements within this summary. The present embodiments may obviate one or more of the drawbacks or limitations in the related art.

DETAILED DESCRIPTION

Figure 1:
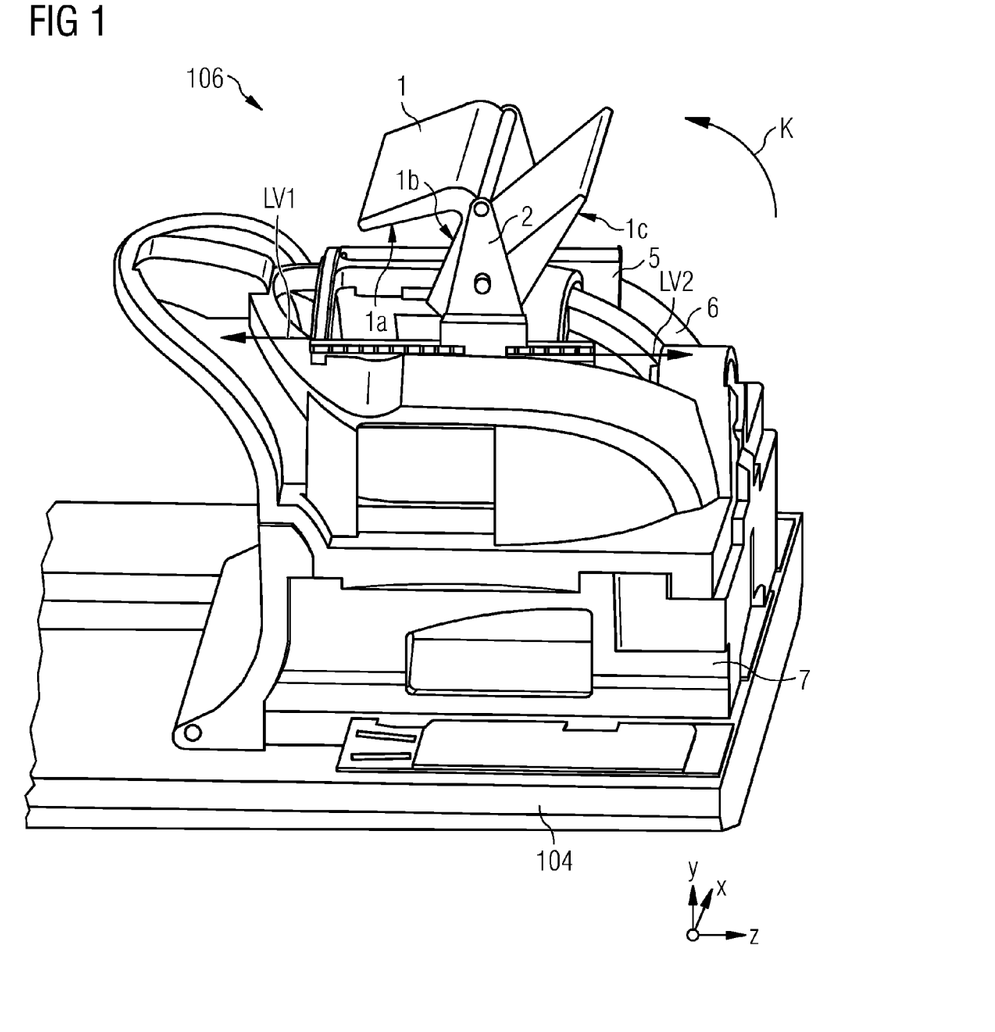
FIG. 1 depicts an embodiment of a head/neck coil, not in a tilted state with respect to patient couch and including a mirror arrangement, in an oblique perspective view from above.
Figure 2:
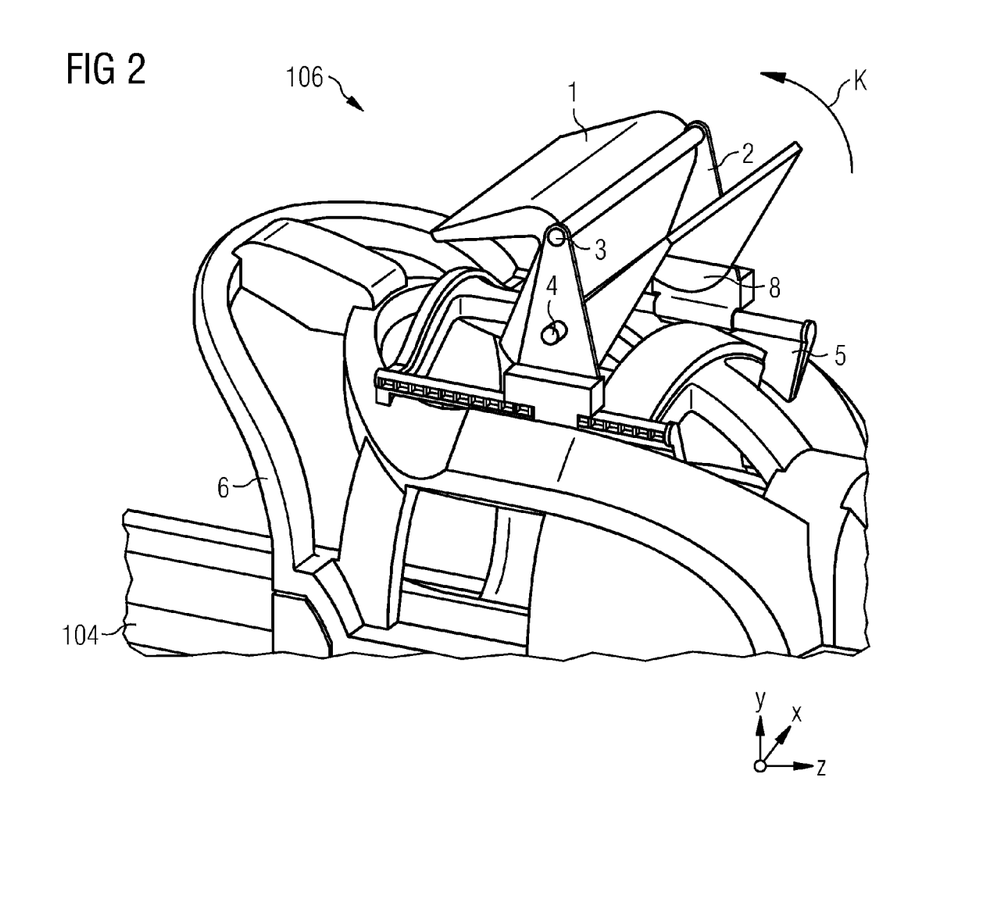
FIG. 2 depicts an embodiment of a head/neck coil, not in a tilted state with respect to patient couch and including a mirror arrangement, in an oblique perspective view from above.
Figure 3:
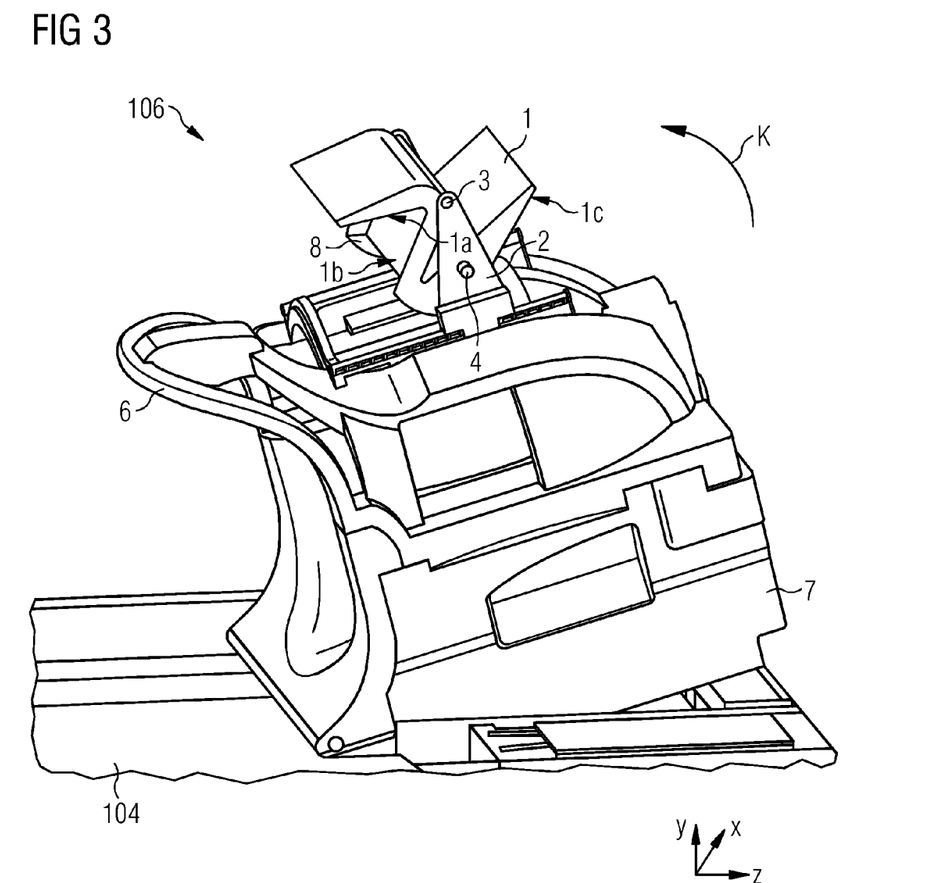
FIG. 3 depicts an embodiment of a head/neck coil, in a tilted state with respect to patient couch and including a mirror arrangement, in an oblique perspective view from above.
Figure 4:
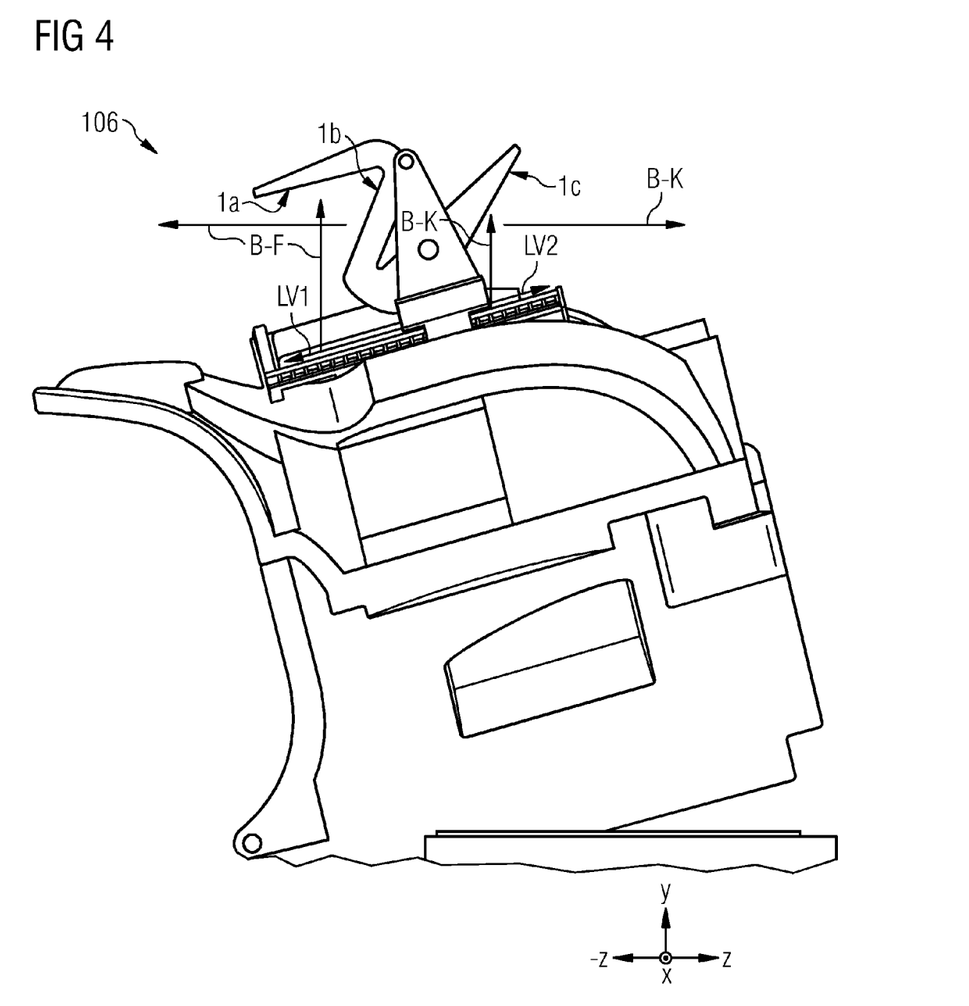
FIG. 4 depicts an embodiment of a side view of a tilted head/neck coil including a mirror arrangement.
Figure 5:
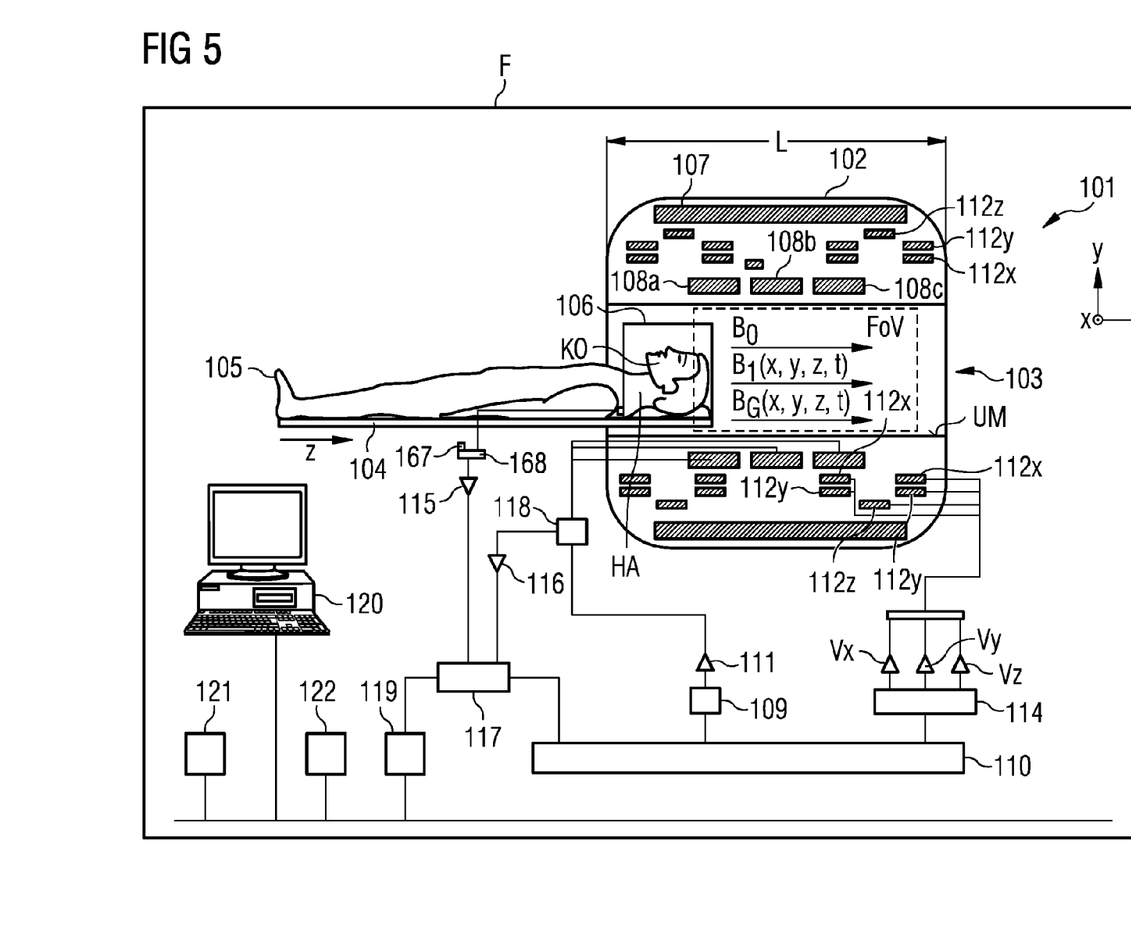
FIG. 5 schematically depicts an embodiment of a MRI system.

FIG. 5 depicts a magnetic resonance imaging device MRI 101 (situated in a shielded room or Faraday cage F) with a whole body coil 102. The MRI device includes a tubular space 103 in which a patient couch 104 with a body of, e.g., an examination object 105 (e.g., of a patient) (with or without local coil arrangement 106) may be driven in the direction of the arrow z in order to generate recordings of the patient 105 by an imaging method. In this case, a local coil arrangement 106 is arranged on the patient in a local region (also referred to as field of view or FOV) of the MRI, by which recordings of a portion of the body 105 in the FOV may be generated. Signals of the local coil arrangement 106 may be evaluated (e.g., converted into images, stored or displayed) by an evaluation device (168, 115, 117, 119, 120, 121, etc.) of the MRI 101. The evaluation device may be connected to the local coil arrangement 106 by, for example, coaxial cables, or by a radio link (167), etc.

In order to use a magnetic resonance imaging device MRI 101 to examine a body 105 (an examination object or a patient) by magnetic resonance imaging, different magnetic fields, which are precisely matched to one another in terms of their temporal and spatial characteristics, are radiated onto the body 105. A strong magnet (e.g., a cryomagnet 107) in a measurement cabin with an opening 103, which may be tunnel-shaped, generates a strong static main magnetic field $B_0$. The magnetic field $B_0$ may have a strength of 0.2 Tesla to 3 Tesla, or more. A body 105 to be examined is, while supported by a patient couch 104, driven into a region of the main magnetic field $B_0$. The region of the magnetic field $B_0$ is approximately homogeneous in the observation region field of view (FoV). The nuclear spins of atomic nuclei of the body 105 are excited by magnetic radiofrequency excitation pulses $B1(x, y, z, t)$. The excitation pulses are radiated in by a radiofrequency antenna (and/or, optionally, a local coil arrangement) depicted here in a simplified manner as (e.g., multi-part=108a, 108b, 108c) body coil 108. By way of example, radiofrequency excitation pulses are generated by a pulse generation unit 109, which is controlled by a pulse sequence control unit 110. After amplification by a radiofrequency amplifier 111, the excitation pulses are conducted to the radiofrequency antenna 108. The radiofrequency system depicted here is merely indicated schematically. In a magnetic resonance imaging device 101, use is often made of more than one pulse generation unit 109, more than one radiofrequency amplifier 111 and several radiofrequency antennas 108a, b, c.

The magnetic resonance imaging device 101 furthermore includes gradient coils $112x$, $112y$, $112z$, by which magnetic gradient fields BG (x, y, z, t) are radiated in during a measurement for selective slice excitation and for spatial encoding of the measurement signal. The gradient coils $112x$, $112y$, $112z$ are controlled by a gradient coil control unit 114 (and, optionally amplifiers Vx, Vy, Vz). The control unit 114, like the pulse generation unit 109, is connected to the pulse sequence control unit 110.

Signals emitted by the excited nuclear spins (e.g., of the atomic nuclei in the examination object) are received by the body coil 108 and/or at least one local coil arrangement 106. The signals are amplified by associated radiofrequency preamplifiers 116 and processed further and digitized by a reception unit 117. The recorded measurement data are digitized and stored as complex numbers in a k-space matrix. An associated MR image may be reconstructed from the k-space matrix filled with values by a multidimensional Fourier transform.

For a coil that may be operated both in transmission mode and in reception mode, such as, e.g., the body coil 108 or a local coil arrangement 106, the correct signal transmission is regulated by an upstream transmission/reception switch 118.

An image processing unit 119 generates an image from the measurement data that is displayed to a user by an operating console 120 and/or stored in a storage unit 121. A central computer unit 122 controls the individual installation components.

In MR imaging, images with a high signal-to-noise ratio (SNR) may be recorded these days using so-called local coils 106 (also referred to as local coil arrangements, coils, local coils). The local coil arrangements are antenna systems that are attached in the direct vicinity on (e.g., anterior) or under (e.g., posterior) the patient. During a MR measurement, the excited nuclei induce a voltage in the individual antennas of the local coil arrangement 106, which is amplified using a low-noise preamplifier (e.g., LNA, preamp) and transmitted by cables to the reception electronics. In order to improve the signal-to-noise ratio in the case of high resolution images, use is made of so-called high-field installations (e.g., 1.5 T to 12 T and more). Since more individual antennas may be connected to a MR reception system than receivers available, a switching matrix (referred to as RCCS here) is installed between reception antennas and receivers. The matrix routes the currently active reception channels (e.g., those that currently lie in the field of view of the magnet) to the available receivers. As a result, it is possible to connect more coil elements than receivers available because, in the case of a whole body cover, it is only necessary to read coils that are situated in the FoV or in the homogeneous volume of the magnet.

An antenna system, which may include of one or more antenna elements (e.g., coil elements, array coil), may be referred to as a "coil" (also referred to as local coil or local coil arrangement). These individual antenna elements may be embodied as loop antennas (e.g., loops), butterfly coils, or saddle coils. A coil includes the coil elements, the preamplifier, further electronics (e.g., standing wave traps, etc.) and wiring, the housing, and, optionally, a cable with plug by which the local coil arrangement is connected to the MR installation. The receiver (RX) attached to the installation side filters digitizes the signal received from the local coil and transmits the data to the digital signal processor. The processing device may derive an image or spectrum from the measurement and make the image or spectrum available to the user for the diagnosis.

A mirror may provide the patient 105 with the option of looking out of the bore 103 of a MRI installation 101 during the imaging MRI examination. The mirror may reduce a feeling of constricted space by providing a certain amount of vision out of the bore 103. A further function of the mirror is the transmission of optical stimulation to the patient within the scope of functional MRIs.

For increasing the patient comfort or for better support of patients with restricted movement in the region of the cervical spine, head coils may be configured to be tiltable. This may result in a rigid mirror, (e.g., a mirror attached to the coil upper part in the case of head examinations), also being tilted. As a result, the (at least one) direction of view (e.g., the direction of view B-F in the direction of the feet or B-K in the direction beyond the head of the patient) provided by the mirror may no longer be horizontal for the patient. As such, the field of view does not lead to the outside through the bore openings but may point to the bore ceiling, base, or to the body of the patient. The direction of view may, in this case, physically refer to photons/waves moving from objects to the eye of the patient in the direction counter to the direction of view, which patient may therefore see the objects by looking in this direction of view.

Head coils were previously not tiltable or individual mirror glasses were adjusted by hand with much outlay, where the operating staff has difficulties in estimating the view of a patient.

FIGS. 1-4 provide details of exemplary embodiments of local coil arrangements.

The following text describes a leveling mirror (system) 1, 2 that may hold itself in a level position (with respect to the direction of view of a patient provided by the leveling mirror) and sets a horizontal (z, −z) direction of view, provided by the system of the leveling mirror 1, 2, for a patient 105. The leveling mirror 1, 2 may hold itself in a level position even if there is an angular adjustment of a head coil (such as a head/neck coil here 7) by tilting K (e.g., with respect to a patient couch 104 and/or a base of the local coil).

A leveling mirror 1, 2 with, e.g., a plurality of (partial) mirrors (such as 1a, 1b, 1c in this case) may be configured in such a way that a patient 105 may look out of the bore 103 of the MRI device 101 in at least two (e.g., opposite) directions (such as in the direction of his feet and beyond his head) and is provided in each case with upright images from the surroundings of the MRI device. To this end, the view B-F in the direction of the feet is deflected, e.g., twice (by mirrors 1a, 1b) (e.g., by 22.5° from the horizontal and 45° between the mirrors 1a, 1b) and the view B-K beyond the head KO is deflected, e.g., once by 45°.

In this case, the leveling mirror system 1, 2 includes a mirror housing 1 with, e.g., three partial mirrors 1a, 1b, 1c (with in this case flat surfaces) and a mirror stand 2.

The mirror housing 1 and a mirror stand 2 (secured to the upper part of the local coil) are mounted in a manner rotatable with respect to one another at the center of rotation 3, for example, by a low-friction plain bearing with a non-magnetic embodiment or a ball bearing with a non-magnetic embodiment. Here, the center of rotation 3 is selected in such a way that, in respect of distance, the center of rotation lies over the center of gravity of the mirror housing 1 and, in respect of position, the center of rotation lies (e.g., exactly) over the center of gravity of the mirror housing 1.

Moreover, provision is made here for a locking screw 4 that may be screwed into a thread in the mirror stand 2. As a result, the mirror stand is adjustable in the screwing-in direction thereof and, when incident on the mirror housing 1, locks both parts 1, 2 with respect to one another, and therefore also locks the angular setting of the mirror housing 1 relative to the mirror stand 2.

The end face of the locking screw 4 may be equipped with an elastic material in order to increase the clamping effect and avoid damage to the surface of the mirror housing 1. In order to improve a side-independent operation of the locking, locking screws 4 may be attached to both sides of the mirror stand 2, wherein only one may suffice for locking. Locking is advantageous since vibrations during the MRI measurements would distort the mirror images. By way of example, the mirror stand 2 is attached to a mirror holder 5 or directly to the head coil upper part 6 (e.g., of the tiltable part 7 of the head/neck coil) and, in this case, displaceable in the patient longitudinal direction (e.g., in the directions LV1 and LV2). This displaceability is advantageous for ideally placing the mirror for each patient 105.

When the head coil (e.g., or the tiltable part 7) is tilted (K), the locking screw may be released so that the mirror housing 1 is free to move. As a result of the inherent weight thereof, the mirror housing 1 will move around the center of rotation 3 and the center of gravity will set under the center of rotation 3 (e.g., corresponding to a plumb bob). As a result, the horizontal direction of view is set and may be locked. The effect of leveling in the horizontal direction z, −z may be made more functionally secure and sped up by additional weights 8 attached on both sides below the point of rotation 4. As a result, friction in the rotary joint 4 may become less influential and the center of gravity of the mirror housing 1 may be lowered.

Scales between the mirror housing 1 and the mirror stand 2 may make the angular setting optically visible and measurable.

Possible developments and advantages of embodiments of local coils may include one or more of the following features. (1) The arrangement may include a rotatably mounted leveling mirror. (2) The arrangement may include an optionally split, rotatably mounted mirror housing 1 and a stationary mirror stand 2. (3) The mirror housing 1 may level itself (e.g., plumb bob) as a result of its weight. (4) The center of rotation 3 may be placed over the center of gravity of the mirror housing 1. (5) The center of rotation 3 may be positioned with respect to the center of gravity of the mirror housing 1 in such a way (e.g., perpendicularly thereover) that the direction of view B-F, B-K of the patient 105 extends horizontally (z, −z) out of the bore 103 in the rest position of the mirror housing 1 when the head coil 7 is not tilted (K). (6) The mirror stand 2 may be displaceable (LV1, LV2) along the mirror holder 5 or the head coil upper part 6. (7) A locking screw 4 may lock the mirror housing 1 during an imaging MRI measurement such that the position of the mirror housing 1 is not influenced by vibrations. (8) Locking screws 4 may be attached to both sides of the mirror housing and/or mirror stand for operation from the left-hand or right-hand side. (9) An elastic coating on the locking screw 4 may increase the clamping effect of the locking. (10) The rotary joint 3 may be of a low-friction type. (11) The complete mirror system may include non-magnetic material. (12) Additional weights 8 may be attached as far as possible below the center of rotation 3 and therefore also lower the center of gravity of the mirror housing 1. (13) Additional weights 8 may be realized, for example, in the form of increased wall strengths of the mirror housing 1. (14) Additional weights 8 may stabilize the leveled state of the mirror system and lead to faster setting thereof. (15) Additional weights 8 may counteract the influence of friction in a rotary joint 3.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A local coil arrangement for a magnetic resonance imaging (MRI) system, the local coil arrangement comprising:
    a head local coil or a head-and-neck local coil; and
    a mirror housing comprising three mirrored surfaces, wherein the mirror housing is mounted in a rotatable manner to the head local coil or the head-and-neck local coil,
    wherein the head local coil or the head-and-neck local coil is configured to move from a non-titled position to a titled position, the non-titled position defined by a base of the head local coil or the head-and-neck local coil being positioned in a plane parallel with a patient couch, and the titled position being defined by the base of the head local coil or the head-and-neck local coil being positioned in a separate plane that is not parallel with the patient couch, and
    wherein the mirror housing is configured to rotate, based on gravity forces acting upon the mirror housing, to maintain a position with respect to, and provide a first view along a first horizontal direction and provide a second view along a second horizontal direction opposite the first horizontal direction, the first and second horizontal directions being in a plane parallel with the patient couch regardless of whether the head local coil or the head-and-neck local coil is positioned in the non-titled position or the titled position.

2. The local coil arrangement as claimed in claim 1, wherein the mirror housing is mounted in a suspended manner.

3. The local coil arrangement as claimed in claim 1, further comprising:
    a mirror stand secured to an upper portion of the head local coil or the head-and-neck local coil,
    wherein the mirror housing is mounted in a rotatable manner on the mirror stand.

4. The local coil arrangement as claimed in claim 1, wherein a first mirrored surface and a second mirrored surface of the three mirrored surfaces are part of a first mirror system, and wherein a third mirrored surface of the three mirrored surfaces is part of a second mirror system.

5. The local coil arrangement as claimed in claim 1, wherein the first horizontal direction is in a direction of a patient's feet.

6. The local coil arrangement as claimed in claim 4, wherein the first mirrored surface of the first mirror system comprises a degree of deflection of 22.5° from the first horizontal direction in a direction of a patient's feet, and the first and second mirrored surfaces of the first mirror system comprise a combined degree of deflection of 45° from the first horizontal direction between the first and second mirrored surfaces.

7. The local coil arrangement as claimed in claim 1, wherein the second horizontal direction is in a direction beyond a patient's head.

8. The local coil arrangement as claimed in claim 4, wherein the third mirrored surface of the second mirror system comprises a degree of deflection of 45° from the second horizontal direction in a direction of a patient's head.

9. The local coil arrangement as claimed in claim 1, further comprising:
    a mirror stand secured to an upper portion of the head local coil or the head-and-neck local coil,
    wherein the mirror housing is mounted on the mirror stand in the rotatable manner at a center of rotation.

10. The local coil arrangement as claimed in claim 9, wherein the mirror housing is mounted on the mirror stand with a low-friction plain bearing or a ball bearing.

11. The local coil arrangement as claimed in claim 9, wherein the center of rotation is positioned at a distance over a center of gravity of the mirror housing, and
    wherein the distance is sufficient for tilting of the head local coil or the head-and-neck local coil and is not prevented by the mount at the center of rotation for the mirror housing to be able to provide the first view along the first horizontal direction and the second view along the second horizontal direction regardless of whether the head local coil or the head-and-neck local coil is positioned in the non-titled position or the titled position.

12. The local coil arrangement as claimed in claim 9, wherein the center of rotation is positioned above a center of gravity of the mirror housing.

13. The local coil arrangement as claimed in claim 12, wherein the center of rotation is positioned vertically over the center of gravity of the mirror housing such that a direction of view of a patient extends horizontally out of a bore of the MRI system when the head coil is in a non-tilted position.

14. The local coil arrangement as claimed in claim 3, further comprising:
  a locking screw, the locking screw configured for locking an angular setting of the mirror housing relative to the mirror stand.

15. The local coil arrangement as claimed in claim 14, wherein the locking screw comprises an end face comprising elastic material.

16. The local coil arrangement as claimed in claim 3, further comprising:
  a first locking screw provided on a first side of the mirror stand, and second locking screw provided on a second side of the mirror stand, wherein the first and second locking screws are configured for locking an angular setting of the mirror housing relative to the mirror stand.

17. The local coil arrangement as claimed in claim 3, wherein the mirror stand is attached to a mirror holder, an upper part of the head local coil or the head-and-neck local coil, or the mirror holder and the upper part of the head local coil or the head-and-neck local coil,
  wherein the mirror stand is displaceable in a patient longitudinal direction, independently of whether the head local coil or the head-and-neck local coil is positioned in the non-titled position or the titled position, and
  wherein the mirror stand is displaceable in a direction inclined with respect to the patient longitudinal direction by a degree of tilt with respect to the patient couch.

18. The local coil arrangement as claimed in claim 3, further comprising:
  scales on the mirror housing, the mirror stand, or the mirror housing and the mirror stand, wherein the scales display the angular setting of the mirror housing and the mirror stand relative to one another.

19. The local coil arrangement as claimed in claim 1, wherein the mirror housing is mounted in a rotatable manner on a mirror stand of the local coil arrangement,
  wherein the mirror housing, the mirror stand, and the three mirrored surfaces consist of non-magnetic material.

20. A local coil arrangement for a magnetic resonance imaging (MRI) system, the local coil arrangement comprising:
  a head local coil or a head-and-neck local coil;
  a mirror housing that is mounted in a rotatable manner to the head local coil or the head-and-neck local coil; and
  weights attached below a center of rotation on one side or on both sides of the mirror housing, wherein the weights are configured to provide increased wall strength of the mirror housing in comparison to other regions of the mirror housing.

21. A local coil arrangement for a magnetic resonance imaging (MRI) system, the local coil arrangement comprising:
  a head local coil or a head-and-neck local coil; and
  a mirror housing comprising a plurality of mirrors, wherein the mirror housing is mounted in a rotatable manner to the head local coil or the head-and-neck local coil,
  wherein the head local coil or the head-and-neck local coil is configured to move from a non-titled position to a titled position, the non-titled position defined by a base of the head local coil or the head-and-neck local coil being positioned in a plane parallel with a patient couch, and the titled position being defined by the base of the head local coil or the head-and-neck local coil being positioned in a separate plane that is not parallel with the patient couch,
  wherein the mirror housing is configured to rotate, based on gravity forces acting upon the mirror housing, to maintain a position with respect to, and provide a first view along a first horizontal direction and provide a second view along a second horizontal direction opposite the first horizontal direction, the first and second horizontal directions being in a plane parallel with the patient couch regardless of whether the head local coil or the head-and-neck local coil is positioned in the non-titled position or the titled position, and
  wherein one mirror of the plurality of mirrors comprises a degree of deflection of 22.5° from the first horizontal direction in a direction of a patient's feet, and two mirrors of the plurality of mirrors comprise a degree of deflection of 45° from the first horizontal direction between the two mirrors.

* * * * *